(12) United States Patent
Rubbert

(10) Patent No.: US 9,539,070 B2
(45) Date of Patent: *Jan. 10, 2017

(54) METHOD AND DEVICE FOR CARRYING OUT OPTICAL PICKUP

(71) Applicant: ORAMETRIX, INC., Richardson, TX (US)

(72) Inventor: Rudger Rubbert, Berlin (DE)

(73) Assignee: ORAMEXRIX, INC., Richardson, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/499,088

(22) Filed: Sep. 27, 2014

(65) Prior Publication Data
US 2015/0164621 A1   Jun. 18, 2015

Related U.S. Application Data

(62) Division of application No. 09/254,078, filed on May 3, 1999, now Pat. No. 9,039,418.

(51) Int. Cl.
| | |
|---|---|
| G01B 11/24 | (2006.01) |
| A61C 9/00 | (2006.01) |
| A61B 1/00 | (2006.01) |
| A61B 1/045 | (2006.01) |
| A61B 1/06 | (2006.01) |
| A61B 1/247 | (2006.01) |
| A61B 5/00 | (2006.01) |
| A61C 19/04 | (2006.01) |
| G01B 11/25 | (2006.01) |
| H04N 1/00 | (2006.01) |

(52) U.S. Cl.
CPC .......... *A61C 9/0053* (2013.01); *A61B 1/00193* (2013.01); *A61B 1/045* (2013.01); *A61B 1/0623* (2013.01); *A61B 1/247* (2013.01); *A61B 5/0088* (2013.01); *A61C 19/04* (2013.01); *G01B 11/2518* (2013.01); *G01B 11/2531* (2013.01); *H04N 1/00026* (2013.01); *A61B 5/4547* (2013.01)

(58) Field of Classification Search
CPC ............. A61C 9/00; A61C 5/00; H04N 5/243; H04N 5/232; G01B 11/24
See application file for complete search history.

(56) References Cited

U.S. PATENT DOCUMENTS

| | | | | |
|---|---|---|---|---|
| 5,175,601 A | * | 12/1992 | Fitts ................... | G01B 11/2513 250/237 G |
| 5,309,243 A | * | 5/1994 | Tsai ..................... | H04N 1/4072 348/221.1 |
| 5,372,502 A | * | 12/1994 | Massen ................. | G01B 11/24 433/215 |

* cited by examiner

*Primary Examiner* — Tarifur Chowdhury
*Assistant Examiner* — Jamil Ahmed
(74) *Attorney, Agent, or Firm* — Jasvantrai C. Shah

(57) ABSTRACT

Disclosed is an optical imaging method and device enabling display and 3D measurement of tridimensional objects (1), whereby at least two individual images are captured one after the other and the image conversion is controlled or regulated differently for these individual images. By employing adjustable optical means (10-14) for the illumination of the object or in the optical path for the imaging of the object on the image converter (15) it is possible to acquire a larger amount of visual information on the object observed than that which is available in an individual image due to the limitations imposed by the design of the converter used (15). The invention relates to processes and design forms of the device enabling recording units to be designed, using simply and generally commercial components, which are able to display and measure larger objects (1) despite a reduced field of vision imposed by the design. This is especially useful for diagnosis in invasive applications in the bodies of humans or animals.

11 Claims, 1 Drawing Sheet

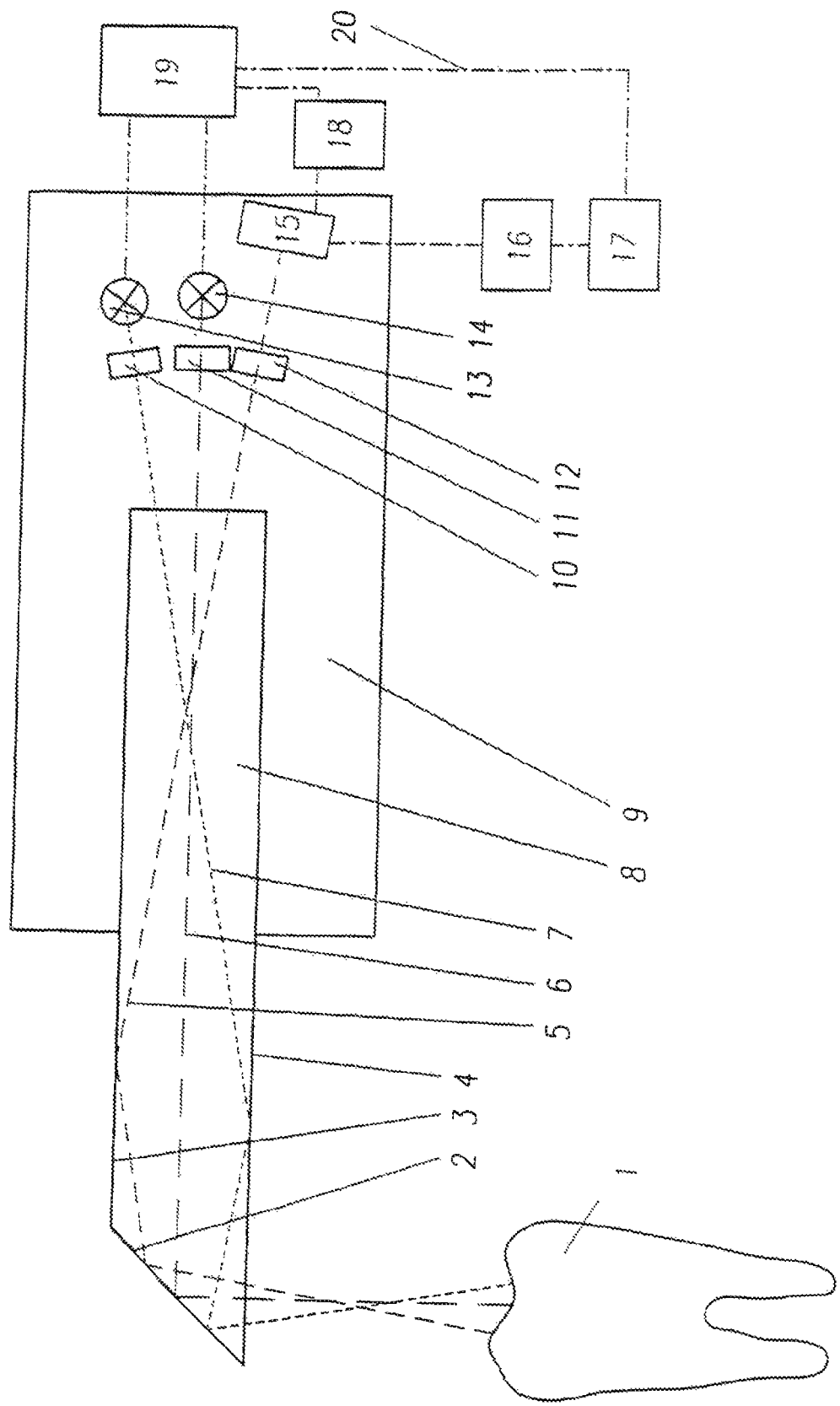

METHOD AND DEVICE FOR CARRYING OUT OPTICAL PICKUP

CROSS-REFERENCE TO RELATED APPLICATIONS

This application is a divisional application of the pending U.S. patent application Ser. No. 09/254,078, filed May 3, 1999, which is based on PCT/DE97/01796 filed Aug. 19, 1997 which is based on German Application 196 36 354.32 filed Sep. 2, 1996, and related to U.S. patent application Ser. No. 10/992,325, filed Nov. 18, 2004, now issued as U.S. Pat. No. 7,751,871, the contents of each of which applications are fully incorporated by reference herein.

The invention relates to a method for carrying out optical pick up, in which at least two single pick ups follow one another consecutively and the amount of beam energy effective for the image conversion is set differently for the single pick ups. The invention further relates to a device for such a method.

For the purposes of representation, documentation or surveying, the range of methods which work on optical principles, offer a large number of advantages. A survey can be done rapidly and without contact. Electronic image converters, for example CCD arrays are known from the prior art, the output signals of which can be stored or evaluated directly after being digitised.

Methods and devices for representing and for optical three-dimensional surveying of spatial surfaces are known. They are based on triangulation methods wherein point, line or any other patterns are projected at a specific angle onto the surface viewed, and the projected patterns are picked up from another viewing angle with an optical system and an image converter. The known geometry between the direction of projection and pick up direction allows the three-dimensional calculation of interpolation points on the surface.

In the field of dentistry, for example, under the commercial name of CEREC, a system for manufacturing ceramic inlays is known, in which an optical 3D measuring device is used in order to survey a cavity in a tooth.

For orthodontic applications, an intra-oral stereo camera is described in German patent application P 42 18 219. This is used as a part of a medical device, sold under the commercial name of "bending art system". The spatial data which are obtained with the aid of this camera from stereoscopic partial pick ups of the set of teeth are subsequently combined with one another and assembled to form overall spatial data about the set of teeth.

When optical methods are used for surveying and documentation purposes, problems do arise, however, when the surface to be determined has unfavourable reflection properties. When producing pick ups of teeth, for example, there is sometimes the task of determining both dark, matt amalgam fillings and also strongly reflecting gold fillings to the same extent with a sufficient data content. In addition, the dynamic range of inexpensive CCD arrays is limited.

The object of the invention is therefore to provide the method and the device for carrying out optical pick up of the type described in the introduction, which make possible the determination of a larger amount of image data about the object being viewed, than is available in a single image because of the limits due to the type of construction of the at least one image converter used.

The object is attained according to the invention, with respect to the method, in that a) a pick up procedure is carried out using at least one areal electronic image converter, in the course of which at least two single images are obtained, and b) the amount of beam energy effective for image conversion is set differently for the single pick ups.

The "amount of beam energy" is understood, within the meaning of this invention, as meaning the integral of the product of the effective duration and intensity of radiation.

Influencing the "amount of beam energy effective for image conversion" is understood, within the meaning of this invention, exclusively as meaning intentional influencing of the amount of beam energy effective for image conversion on the part of the means of the pick up device itself. The fact that in addition the object to be determined itself substantially—and in the course of the pick up procedure, differently—influences this amount of beam energy effective for image conversion is obvious.

The amount of beam energy effective for the single pick ups can advantageously according to the invention be changed in different manners, in that a) at least one beam source is set differently with respect to its intensity and/or effective duration for the pick up of the single images; b) optical means are set in at least one beam path between a beam source and the object to be determined such that the intensity and/or the effective duration of the beam energy for illuminating and/or transilluminating the object is changed for the pick up of single images; c) optical means are set in at least one beam path between the object and the image converter such that the intensity and/or the effective duration of the beam energy reflected or not absorbed by the object is changed for the pick up of single images; d) so-called shutter means of the image converter are controlled such that the effective time duration of the optoelectronic conversion of the beam energy used for image conversion in the image converters is set differently for the single pick ups.

A beam source, within the meaning of this invention, is any direct generator of beam energy. These are, inter alia, means for generating x-rays, visible, infra-red and ultraviolet light.

Optical means in the beam path between the beam source and object, or between the object and image converter which allow the intensity and/or the effective duration of the beam energy for illuminating/transilluminating the object or for irradiating the image converter for picking up the single image to be set differently are, within the meaning of this invention, optical means which change the intensity of the beam energy—except for fringe effects—regularly for the whole area, that is to say, for example aperture means and mechanical and LCD shutters. Optical means which project patterns onto the surface of the object in a changeable manner do not fall within this definition.

Pick up units are known in which aperture means or shutter means are designed to be adjustable in image converters. It is known from the prior art to control these means in automatic control loops for controlling the lighting in the manner such that the lighting of the single pick ups is optimised. The term "set differently for the single pick ups" means, within the meaning of this invention, that the means described hereinabove for consecutive pick ups are set differently in order to intentionally vary the content of the image data of consecutive single images during the course of the pick up procedure.

In a particularly advantageous configuration of the invention, at least one beam source is set differently with respect to its intensity for the single pick ups.

It is advantageous according to the invention, in addition or alternatively to the adjustable beam source, to bring an adjustable aperture means, optionally with a suitable optical system, into the optical beam path, which can be set differently with respect to the opening time and/or focal length for the single pick ups. This aperture means can, to an equal measure, advantageously be arranged in the optical beam path between a beam source and the object, or between the object and the image converter.

Alternatively, according to the invention, instead of the aperture means, for example, a mechanical shutter or an LCD means can be arranged which can be set differently for the single pick ups. Advantageously, according to the invention, the LCD means can be set to be transparent over its surface area, partially transparent, or opaque.

So-called shutter means of CCD image converters are known from the prior art, with the aid of which the cycle time for shifting the charges from the areas of the CCD array provided for lighting into optically covered areas can be selected such that the integration time of the image converter and thereby the brightness of the image picked up can be changed. Accordingly, it is advantageous according to the invention to differently set the amount of beam energy effective for image conversion by means of a suitable controlling of this means for single images.

A particularly advantageous configuration of the invention provides that the single image data obtained is digitised, and the digitised data are made available to a device for electronic data processing.

Some commercially available CCD arrays are, for example operated at an image refresh rate of 50 Hz, that is to say fifty pick ups or recordings per second are made. It is known from the prior art to store and to process the images obtained by means of electronic data processing. For example, so-called "frame grabbers" are obtainable inexpensively as plug-in cards for work-place computers, which directly digitise a video signal, convert it into a suitable data format, and make it available to the computer as data in its main memory. That processing can be done in real time.

When in an advantageous manner according to the invention, taking the pick up unit described hereinabove, a lighting source illuminates the object to be determined in a repeated sequence for $\frac{1}{50}$th of a second at low brightness, and subsequently for a further $\frac{1}{50}$th of a second with high brightness, synchronously with the image refresh rate of the CCD array, as a result images are obtained alternately with a low and a strong illumination. The low-lit images will image the parts of the surface with a high degree of reflection satisfactorily, while the parts of the surface with a low degree of reflection are imaged only very dimly and without a substantial data content. By contrast, with the strongly lit images, the weakly reflecting surface portions are imaged sufficiently brightly, and with a high data content, while the strongly reflecting surface parts are generally extremely bright and therefore appear saturated.

It is particularly advantageous according to the invention to control the optical means described for influencing the amount of beam energy effective for image conversion synchronously with the image refresh rate.

It is additionally particularly advantageous according to the invention when the data belonging to at least two single images are partially or completely combined in the means for electronic data processing by means of suitable algorithms.

For example, it is advantageously possible according to the invention to combine the digitised data of two consecutive images by means of appropriate software such that the image areas with a high degree of reflection are selected from the low-lit single image described hereinabove, and the image areas with a low degree of reflection are selected from the strongly lit single image described hereinabove, and are transformed in a common brightness scale. As a result, an image is obtained which represents all image areas with sufficient contrast.

It is advantageous according to the invention to provide finer stepping of the strength of illumination. In this case, further brightness steps can be used. The combined image is then composed from the image data of a plurality of single images.

According to the invention it is not necessary to evaluate exclusively images which follow one another directly, or to combine only single images which have been taken using different beam energy.

It is particularly advantageous according to the invention to have automatic control of the optical means described for influencing the amount of beam energy effective for image conversion, dependent upon evaluation of the actual reflection ratios in the images previously picked up of the respective surface. By means of this control loop, it is ensured according to the invention that the respective illumination strength is optimised for all areas of the object to be determined.

The use of a plurality of beam sources is also advantageous according to the invention. For example, by means of a beam source and suitable optical means, a pattern can be projected onto the object to be surveyed. When the angle of projection is different from the angle of pick up, in a known manner 3D data can be calculated from the imaging of the pattern on the image converter. The other beam source then alternately completely illuminates the surface to be surveyed. In this way both 3D information and views of the surface being determined can be obtained from the single images. The advantage according to the invention is in that a corresponding device, without mechanical movement of the optical means, can be designed with a simple configuration in regard to the beam path and using commercially available components.

In this manner, according to the invention optical beam paths can advantageously be switched to be active and inactive, both for illumination and/or transillumination of the object to be determined and for the imaging of the object on the image converter or converters by control of the optical means designated as being suitable in this invention (for example, adjustable beam sources or aperture means, optionally with suitable optical systems).

A further advantageous configuration of the invention uses at least two beam sources and at least two image converters, wherein by means of suitable optical means, for example by means of a beam splitter, the respective image data are projected onto both image converters. When one of the two image converters is not set for visible light, but instead, for example, for infra-red or ultra-violet light, and one of the two beam sources also delivers such light, by alternating control of one or the other beam source, and by appropriate selection of the image signal of the corresponding image converter, image data from the visible light range and image data from an invisible range can be acquired alternately.

In this connection it is advantageously possible according to the invention to display the data of the image converter for visible light on a monitor, and to process the data of the image converter for invisible light by data processing such that they can also be represented on the monitor in a meaningful form. When infra-red light is used, the different strengths of signals obtained can be distinguished, for example, by different colours, as is usual when infra-red images are evaluated for testing the heat radiation of buildings. The user can then choose between the colour and contrast image and the evaluation of the invisible beams for representation on the monitor.

A further advantageous configuration of the invention uses at least one beam source with an extremely short duration of illumination, preferably in the range from 0.001 to 0.01 seconds, and high brightness. The amount of energy radiated for lighting the object to be determined can, in this instance, be varied by the duration of the beam. In addition, the influence of shaking effects when the pick up device is handled carelessly, is minimised. Such beam sources are, for example, known in the form of a stroboscopic light, flash lamp, flash tube or flash LED, and are, for example, used (also pulsed externally) for adjusting the ignition timing of four-stroke engines with mechanical contact breakers.

During the pick up procedure, "shaded" areas can occur when the surface to be determined has undercuts with respect to the beam path of the projected pattern. In this sense, undercuts are configurations of formations of the three-dimensional contour which are covered up by parts of the object itself with respect to the direction of view or of projection, and to that extent are not accessible for viewing or projection. For such an instance, it is particularly advantageous according to the invention to provide at least one further beam source which using suitable optical means projects a pattern from a different spatial direction onto the surface, alternately to the other beam sources used. By means of appropriate software, the 3D data about the surface to be surveyed obtained from the different projection angles can be combined such that the 3D data are mutually supplemented.

All the configurations of the method and of the device described in this invention can be combined with one another in many ways particularly advantageously according to the invention.

When surveying places which are difficult to access, the constructional size of the part of the device which is located in the area which is difficult to access is limited. An example of this is for pick up carried out in the oral cavity. For this reason it is not readily possible to make a record of, for example, a complete jaw. If the pick up device according to the invention is now moved relative to the surface being surveyed, different images are obtained as a result. The data processing following the single pick ups then offers the possibility of combining adjacent single images, provided a sufficient degree of overlap of by the single images is ensured.

It is known that a position and alignment of the pick up device which is changed relative to the surface being viewed results in a more or less strong divergence in the images of one and the same surface segment viewed. To this extent, it is known from the prior art to use digital approximation methods for combining and supplementing adjacent images and sequences of images. Suitable digital algorithms allow for partial compensation for the distortion errors of the planar imaging of the real, usually spatially configured surface. The continual combination of planar images of spatial objects is limited, however. The different methods for planar representation of the surface of the earth are a clear example of this.

In this connection, the idea suggests itself that not only the two-dimensional images are combined into a whole image, but also 3D data which are ascertained. Suitable so-called matching algorithms which allow partial data about three-dimensional surfaces, using 3D coordinates of corresponding surface segments, to be combined into overall data are known.

The pre-condition of having corresponding surface segments is set down for the purpose of use for the invention described by way of example hereinabove. As the device according to the invention produces single pick ups every 0.02 seconds when using an image converter with an image refresh rate of 50 Hz, it can be assumed that even when the device is, for example, manually guided for pick up of the tooth set of a patient, each image will be picked up from a similar position to that of the previous pick up, and that a large degree of overlap is thus ensured between two consecutive pick ups, both for 2D data and for the 3D data obtained. A typical size for the part of the surface to be surveyed which is determined within one pick up, is approximately 10 mm×10 mm, so even with a setting with a high speed of movement, a manually guided device, at approximately 30 mm per second, produces a degree of overlap of more than 90%. Even when it is assumed that the possibilities described hereinabove for alternating lighting and evaluation are made use of, and for example only each fourth image is actually taken into account for a three-dimensional calculation, a degree of overlap of more than 75% still results from this.

With such an advantageous configuration of the invention, by moving the device along the row of teeth, with each image evaluated, new data about the three dimensional shape of the surface to be surveyed is added to those already available. In addition, by digital combination of the 3D data relating to the single images, with respect to the respective overlap the resulting data can be optimised. The data are made more accurate by the use of statistical methods, or compressed by increasing the number of interpolation points included. The quantity of the data to be obtained in such a way is not limited by the method or the device itself, but simply by the size of the memory available in the data processing unit.

The use of the beam sources described hereinabove for short beam pulses is particularly advantageously used according to the invention in the connection described hereinabove, in order to minimise shaking effects of a, for example, manually guided pick up device.

The advantageous use, according to the invention, of at least one beam source which, by means of suitable optical means, projects a pattern at a sufficient triangulation angle with respect to the pick up direction onto the surface to be determined, and at least one further beam source, which, for example, alternately illuminates the object in true colour, and the following combination of the 3D data belonging to the single images with the colour data assigned to the single images, allows an extremely realistic colouration of a resulting 3D grid representation.

In the present connection, it is particularly advantageous according to the invention to operate the beam sources which, for example, by means of a condenser, mask and optical system, project a line pattern on the surface to be determined, with a high beam intensity so that the projected pattern is sufficiently light in all areas of the surface for obtaining the 3D information. However, the areas of the surface with a strong reflection contain insufficient contrast and/or colour data for the purpose of a clear representation. The missing data can be supplemented as described hereinabove by combination of single image data which are obtained with reduced lighting, for example from the same beam source or by means of the beam source also described for surface lighting of the surface to be determined.

In the present connection, it is particularly advantageous in accordance with the invention to set the beam energy for the projection of the pattern differently for the single images in order, when the line pattern is picked up—as described hereinabove for surface image pick up—to optimise overall the image data of the line pattern with respect to the partial reflection properties of the surface of the object by combination of the single pick ups.

In this connection it is particularly advantageous according to the invention to use a colour image converter and white light for projection of the line pattern. If the beam energy is now varied as described hereinabove, for example using a flash lamp, the sequence of single images enjoys optimum colour and contrast data along the projected lines as well as optimum contrast signals for the individual lines for calculating the 3D interpolation points. If the pick up device is now moved slowly with respect to the object, by suitable combination of the data assigned to the single images, the 3D data can be compressed and a colour image of the object can be generated without gaps. In this sense, uniform surface illumination of the object as also previously described can be dispensed with.

The device for carrying out optical pick up of the type described in the introduction attains the object according to the invention by means of the features wherein a) at least one areal electronic image converter employing an optical system suitable for pick up of images is used, which is suitable for picking up at least two consecutive images, and b) at least one adjustable optical means is provided, which can be set differently for pick up of the single images with respect to the amount of beam energy effective for image conversion.

A configuration of the device which is particularly advantageous according to the invention provides means which effect digitising of the output signals of the at least one image converter and make these data available to a data processing system.

A configuration of the device which is particularly advantageous according to the invention provides means which can store the data from at least two single images.

A configuration of the device which is particularly advantageous according to the invention provides means which process the data from at least two single images and is able to combine these by means of suitable algorithms.

A configuration of the device which is particularly advantageous according to the invention provides optical means in the beam path between the at least one beam source and the object to be determined, which allow the projection of a pattern.

Further advantages, features and possible applications of the present invention will be evident from the following description of preferred embodiments with reference to the attached drawing.

The attached drawing (FIG. 1) shows a view of a device for carrying out optical pick up according to the invention, partially schematically.

The pick up device according to FIG. 1 is, in order to simplify the description, a reproduced only schematically without known, obvious parts of the device. To simplify the description, a detailed description of embodiments of parts of the device which belong to the prior art, such as specific embodiments of connections or fixing of parts has been dispensed with.

All means (8 and 10 to 15) are rigidly fixed to a base frame (9). The fixing of the carrier (8) with respect to the base frame (9), is releasable and in the embodiment shown here, is such that when put together again, the intended geometrical arrangement of these parts with respect to one another is produced without adjustment. In addition the carrier (8) and the optical means (2 to 4) rigidly connected to it in the embodiment shown here, are of such a configuration that they are suitable for disinfection and sterilisation separately from the remaining means (9 to 20).

The object (1) is a surface with three-dimensional extents. For example, it can be a tooth or a row of teeth of a human set of teeth. At a short distance away there extends the carrier (8) together with its components, and it can easily be imagined that the part of the carrier (8) together with its components, facing towards the object (1), can be accommodated in the oral cavity. It is also easily imaginable that the part of the pick up device composed of the means (2 and 15) is held manually and the user of the device carries out an intraoral pick up procedure of a part of the set of teeth of a patient, shown as the object (1) in FIG. 1.

In the embodiment shown here, the carrier (8) is a prismatic body of optical glass of BK 7 quality with a cross-section of 15 nm×15 mm. The long sides are parallel ground, polished, and are suitable in this embodiment as planar optical deflecting means making use of total reflection, shown in FIG. 1 as mirrors (3 and 4). The part of the glass prism, shown in FIG. 1 as a carrier (8), facing the object (1) is inclined at 45.degree. This surface is also ground, polished and in addition is mirrored and serves as a plane mirror (2) for deflecting the beams in the direction of the object (1).

For reasons of space, it can be advantageous to also arrange deflecting means on the side of the carrier (8), facing away from the object (1), so that the means (10 to 15) do not have to be arranged in one plane.

Within the meaning of the invention, mirrors are optical deflection means regardless of whether the relevant surfaces are mirrored or the capacity for deflecting optical beams takes place by making use of total reflection.

The carrier (8) which is in the form of as a glass prism (8) can, according to the invention, advantageously be heated so that it does not fog when invasive pick ups are carried out. Alternatively, an air stream can be conducted such that the part of the glass body used intra-orally and which is relevant for the pick up is kept dry.

In another advantageous embodiment of the device, the carrier (8) is of such a form that it is suitable for endoscopic examinations. In addition it is advantageous according to the invention possibly to arrange further optical means on the carrier (8), for example lenses, in addition to, or instead of, the mirror (2).

The beam sources (13 and 14) respectively provided with the optical means (10 and 11) serve to light the object (1). The beams are deflected by means of the planar mirrors (2 to 4). In the embodiment shown here, the optical means (10) are composed of a condenser, a mask and an objective. By means of the means (13, 10, 4, 2) a line pattern is projected over its area onto the object (1). A condenser is used as the optical means (11). By means of the means (14, 11 and 2, the object can be illuminated over its area. Flash lamps are used as beam sources (13 and 14). The beam sources (13 and 14) are connected to a control unit (19) by means of electrical connections (20).

The beams reflected from the object (1) are deflected by the mirrors (2 and 3) and imaged by means of the optical means (12) onto the image converter (15). In the embodiment shown here, the optical means (12) are composed of an objective. The electronic image converter (15) is in the form of a CCD array, and is connected via electrical connections (20) to a control means (18) and a means for digitising the output signal of the image converter (16). The digitised image data are made available to a data processing unit (17) via the electrical connection (20). In the embodiment shown here, a so-called frame-grabber with its own signal processor for rapid processing of the image data is used for the unit (16), and a commercially available PC is used for the unit (17).

The electrical connections (20) between the means (18) and (19) and between the means (17) and (19) serve to synchronise the control of the beam sources (13 and 14) with the image refresh rate of the image converter (15) and for returning the image data in a control loop for optimising the controlling of the beam sources.

The means (13, 10 and 4) on the one hand and (15, 12 and 3) on the other hand are aligned with respect to their optical axes (7 and 5) such that between the direction of projection of the pattern and the direction of image pick up, a triangulation angle of 20 degrees is produced. The optical axis (6) for the surface illumination is, in this embodiment, in the bisecting line of the angle of the other two optical axes (5 and 7). In order to obtain data relevant to the 3D calculation, the projected line pattern is played transversely to the plane fixed by the triangulation angle.

In the embodiment shown here, the object (1) is illuminated synchronously to the image refresh rate of the image converter (15) alternately on the one hand with a line pattern, and on the other hand over its surface/uniformly. In the embodiment shown here, the image refresh rate is at 50 Hz.

For optical, three-dimensional determination of, for example, the tooth set of a human, the front part of the carrier (8) together with its components is guided into the mouth of the patient, a pick up procedure is started by means of an actuating element available within the scope of the data processing unit (17), not shown in FIG. 1, and in the course of the pick up procedure the part of the device composed of the means (2 to 15) is guided manually such that gradually all the relevant surface areas of the object (1) are both imaged on the image converter (15) and to an equal extent involved in by the projection of the line pattern. The pick up procedure is terminated by means of a further actuation of the actuating element described hereinabove.

In the sequence of the single image data picked up, there are now alternately images of the line pattern deformed because of the surface shape of the object (1) and images of the areally illuminated object (1). From the deformation of the line pattern, when the optical beam path is known, and taking into account the geometrical configuration of the projected line pattern for the corresponding single image pick ups, 3D coordinates can be calculated for a large number of interpolation points. From the sequence of the image data and 3D coordinates assigned to the single images, both the planar image data and the 3D coordinates can then be combined in the manner described hereinabove, so as a result, despite the viewing field of the pick up unit being of an order of size of 15 mm×15 mm, there are both the 3D coordinates and a homogenous colour image of the whole tooth set. In this respect gaps caused by undercuts, confusing optical reflections or dark image areas without any substantial contrast are no longer present. By means of an on-line calculation and display of the respective intermediate results, the user can also optimise the manual guidance of the pick up device.

The knowledge of the optical beam path and of the geometrical configuration of the projected line pattern, necessary for 3D calculation, is obtained advantageously according to the invention in that a planar object (1), the detailed configuration of which is not shown in FIG. 1, and which also has a line pattern, in transverse relationship to the projected line pattern, is placed in succession at different distances parallel to the surface of the carrier (8) facing the object (1). If two image pick ups are now made, and if the reference object (1) is planar and the geometrical configuration of the line pattern and the distance between the carrier and reference object (1) are known for both pick ups, both the beam path and the geometrical configuration of the projected pattern can be calculated exactly for a large number of interpolation points. The values calculated already take into account any deformations caused by manufacturing tolerances of the means used. The intermediate values can then be further interpolated in the 3D calculation.

The embodiment shown here is distinguished in that, a) no moving parts are used in the pick up unit; b) the optical design is of a simple configuration; c) by using an elongate glass body, a simple possibility has been selected for causing the beams to intentionally reflect, once or more times, off the walls of the glass body to produce a pattern on the surface to be surveyed, so that a larger angular difference is produced relative to the pick up beams than if all the beams were guided in a straight line by means of the carrier, wherein the relative angle of the beams to one another is simply produced as the arcus tangens of the ratio of the distance between the object and the pick up and lighting units on the one hand, and the distance of the optical systems from one another on the other hand. An angular difference in the range between 15.degree. and 45.degree. between the pattern-generating beams and the beams for pick up is advantageous for carrying out the survey. Larger angles increase the risk of "shadow forming" in the case of stepped surfaces, smaller angles reduce the accuracy of the survey, as the evaluation method is based on triangulation calculations; d) except for the carrier (8), base frame (9), mask for projecting the pattern and control units (18 and 19) commercially available hardware components can be used; e) the errors caused by manufacturing tolerances of the means used can be compensated for by means of the "calibration" of the pick up unit described hereinabove and in that respect only low demands overall have to be placed on the manufacturing tolerances of the means used.

LIST OF DESIGNATIONS 1 object 2,3,4 mirror 5,6,7 optical axes 8 carrier (here in the form of a body of optical glass) 9 base frame 10,11,12 optical means (lens system, aperture means, and so forth) 13,14 beam source (here in the form of a flash lamp) 15 electronic image converter (CCD array) 16 means for digitising analog signals (frame grabber) 17 data processing unit (PC) 18 control unit for the image converter 19 control unit for the beam sources 20 electrical connections.

The invention claimed is:
1. A scanner for scanning an object and obtaining three-dimensional information about the surface of said object, comprising:
   a) at least one two-dimensional electronic image converter;
   b) at least one optical element imaging said object on said electronic image converter;
   c) a first beam source for illuminating said object and a second beam source for illuminating said object,
   d) wherein said first beam source illuminates said object and substantially simultaneously a first image of the object is obtained by said at least one electronic image converter, said first image obtained from incident radiation at a first level of received beam energy;

e) wherein said second beam source illuminates said object and substantially simultaneously a second image of said object is obtained by said at least one electronic image converter, said second image obtained from incident radiation at a second level of received beam energy different from said first level; and f) wherein said illumination of said object and the generation of said first and second images are performed in succession such that said electronic image converter thereby obtains two consecutive images of the object at different levels of received beam energy.

2. The scanner of claim 1, wherein said electronic image converter comprises a charge-coupled device array.

3. The scanner of claim 1, wherein said scanner further comprises a carrier which is in the form of a prism adapted for directing radiation from said beam sources in the direction of said object, said prism sized and shaped so as to have a portion thereof fit into the oral cavity of a human and enable said portion to be moved relative to anatomical structures within said oral cavity.

4. The scanner of claim 1, wherein said at least one of said beam sources comprises a flash lamp.

5. The scanner of claim 3, wherein the scanner further comprises a frame housing said first and second beam sources and wherein said carrier is rigidly connected to said frame.

6. The scanner of claim 5, wherein said optical element comprises at least one lens element fixed with respect to said frame.

7. The scanner of claim 5, wherein said carrier further comprises at least one optically reflective surface reflecting radiation from said at least one beam source towards said object.

8. The scanner of claim 7, wherein said reflective surface comprises a peripheral internal surface of said carrier.

9. The scanner of claim 7, wherein said reflective surface comprises at least two internal surfaces of said carrier, and wherein radiation from said beam sources undergoes total internal reflection in a path between said beam sources and said object.

10. The scanner of claim 7, wherein said reflective surface further comprises a mirror.

11. The scanner of claim 5, wherein said carrier is releasable from said frame to thereby permit said carrier to be separately sterilized and/or disinfected from said frame.

* * * * *

UNITED STATES PATENT AND TRADEMARK OFFICE
CERTIFICATE OF CORRECTION

PATENT NO.         : 9,539,070 B2
APPLICATION NO.    : 14/499088
DATED              : January 10, 2017
INVENTOR(S)        : Rubbert It is certified that error appears in the above-identified patent and that said Letters Patent is hereby corrected as shown below:

Assignee:
ORAMEXRIX, INC. should be -- OraMetrix GmbH --

Signed and Sealed this
Seventeenth Day of April, 2018

Andrei Iancu
*Director of the United States Patent and Trademark Office*